(12) United States Patent  (10) Patent No.:     US 6,992,209 B2
Lilga et al.  (45) Date of Patent:     Jan. 31, 2006

(54) METHODS OF FORMING ALPHA, BETA-UNSATURATED ACIDS AND ESTERS

(75) Inventors: Michael A. Lilga, Richland, WA (US); Todd A. Werpy, W. Richland, WA (US); Johnathan E. Holladay, Kennewick, WA (US)

(73) Assignee: Battelle Memorial Institute, Richland, WA (US)

( * ) Notice: Subject to any disclaimer, the term of this patent is extended or adjusted under 35 U.S.C. 154(b) by 373 days.

(21) Appl. No.: 10/315,404

(22) Filed: Dec. 9, 2002

(65) Prior Publication Data

US 2004/0110974 A1    Jun. 10, 2004

(51) Int. Cl.
C07C 69/66     (2006.01)
C07C 67/30     (2006.01)
C07B 35/00     (2006.01)

(52) U.S. Cl. .................. 560/185; 560/212; 562/599
(58) Field of Classification Search ................ 560/185, 560/211, 212
See application file for complete search history.

(56) References Cited

U.S. PATENT DOCUMENTS

| | | |
|---|---|---|
| 3,208,857 A | 9/1965 | Howard et al. |
| 3,487,101 A | 12/1969 | Völker et al. |
| 4,529,816 A | 7/1985 | DeColibus et al. |
| 4,617,405 A | 10/1986 | Kiely et al. |
| 4,729,978 A | 3/1988 | Sawicki |
| 4,786,756 A | 11/1988 | Paprizos et al. |
| 4,975,537 A | 12/1990 | Aristoff et al. |
| 5,068,399 A | 11/1991 | Naito et al. |
| 5,250,729 A | 10/1993 | Abe et al. |
| 5,252,473 A | 10/1993 | Walkup et al. |
| 5,679,832 A | 10/1997 | Stephens |

FOREIGN PATENT DOCUMENTS

DE      4340369 A1 * 10/1994

OTHER PUBLICATIONS

Storey et al., "New Epoxy-Terminated Oligoesters: Precursor to Totally Bio Degradable Networks", 1993, Journal of Polymer Science, Part A: Polymer Chemistry, 31(7), pp. 1825-1838.

Wurtz, A. et al., "Memoire sure L'Acide Lactique" (Report on Lactic Acid), Annals of Chemistry and Physics, 3$^{rd}$ series, 1861, pp. 101-124 (includes translation).

Burns et al., Journal of the Chemical Society, 1935, pp. 400-406.

* cited by examiner

Primary Examiner—Paul A. Zucker
(74) Attorney, Agent, or Firm—Wells St. John P.S.

(57) ABSTRACT

The invention includes a method of forming an alpha, beta-unsaturated compound. A carboxylic acid is mixed with an alpha-hydroxy acid or an alpha-hydroxy ester and is esterified to form an alpha-acyloxy derivative. The alpha-acyloxy derivative is transformed into an alpha, beta-unsaturated derivative. The invention additionally includes a process of forming an acrylate. Lactic acid or a lactic acid ester is reacted with a first portion of acetic acid in the presence of a first catalyst to produce the corresponding 2-acetoxy propionic acid or ester. A non-reacted portion of the acetic acid is recycled. The 2-acetoxy propionic acid or ester is transferred to a second vessel containing a second catalyst, and acetic acid is liberated from the 2-acetoxy propionic acid or ester to produce a corresponding acrylic acid or acrylate ester. The acid or ester is subsequently esterified by reaction with an alcohol to form a desired acrylate ester.

34 Claims, 1 Drawing Sheet

METHODS OF FORMING ALPHA, BETA-UNSATURATED ACIDS AND ESTERS

TECHNICAL FIELD

The invention pertains to methods of derivatizing an alpha-hydroxy group, and methods of forming alpha, beta-unsaturated compounds.

BACKGROUND OF THE INVENTION

Various alpha, beta-unsaturated acids and esters are commercially valuable. Compounds such as acrylic acid and acrylates are used extensively for production of a variety of polymer materials, plastics and super-absorbants.

A number of synthesis methods are currently utilized to produce alpha, beta-unsaturated compounds such as acrylic acid and its ester derivatives. Many of these methods can be expensive, time consuming and/or inefficient. Additionally, for methods that utilize an expensive reagent such as anhydrides, regeneration of the reagent, although possible, is difficult and may be cost prohibitive.

It is desirable to develop alternative methods to generate alpha, beta-unsaturated acids and esters.

SUMMARY OF THE INVENTION

In one aspect the invention pertains to a method of forming an alpha, beta-unsaturated compound by mixing an initial amount of a carboxylic acid with an alpha-hydroxy acid or an alpha-hydroxy ester. A first portion of the initial amount of carboxylic acid is esterified to form an alpha-acyloxy derivative and water. A second portion of the carboxylic acid is recovered in combination with the water produced during the esterification. The alpha-acyloxy derivative is transformed into an alpha, beta-unsaturated derivative and carboxylic acid released during the transformation can be recovered.

In one aspect the invention pertains to a process of forming an acrylate without utilizing an anhydride reagent. Lactic acid or a lactic acid ester is introduced into a first vessel with an excess of acetic acid (as measured by molar value). The lactic acid or lactic acid ester is reacted with a first portion of the acetic acid in the presence of a first catalyst to produce the corresponding 2-acetoxy propionic acid or ester. A non-reacted portion of the acetic acid is recycled and can be re-used for further reaction without converting to an anhydride. The 2-acetoxy propionic acid or ester is transferred to a second vessel where, in the presence of a second catalyst, acetic acid is liberated from the 2-acetoxy propionic acid or ester to produce a corresponding acrylic acid or first acrylate ester. After removing the liberated acetic acid by distillation, the acetic acid or first acrylate ester is mixed with an alcohol and the acrylic acid is esterified, or the first acrylate ester is trans-esterified, by reaction with the alcohol to form a second acrylate ester.

The present invention can be particularly advantageous since it allows utilization of a continuous system for production of alpha, beta unsaturated acids and esters.

BRIEF DESCRIPTION OF THE DRAWINGS

Preferred embodiments of the invention are described below with reference to the following accompanying drawings.

DETAILED DESCRIPTION OF THE PREFERRED EMBODIMENTS

In general, methods according to the present invention can be utilized to produce an alpha, beta-unsaturated compound having formula (I).

Formula (I):

where $R_1$=H or a linear or branched, saturated or unsaturated hydrocarbon group which can optionally contain one or more hetero atoms. Preferably, $R_1$ is H or a hydrocarbon comprising from 1–20 carbons. In particular aspects of the invention, $R_1$ can be selected from the group consisting of H, methyl (Me), ethyl (Et), n-butyl and 2-ethylhexyl. $R_2$ can be H or a linear or branched, saturated or unsaturated hydrocarbon group which can optionally contain one or more hetero atoms. $R_2$ can preferably be H or a hydrocarbon comprising from 1–20 carbons, and more preferably can be H or Me. $R_3$ and $R_4$ can be individually selected from the group consisting of H and linear or branched, saturated or unsaturated hydrocarbons which can optionally contain one or more hetero atoms. Preferably, $R_3$ and $R_4$ are individually H or a hydrocarbon having from 1 to 20 carbon atoms, and most preferably $R_3$ and $R_4$ are independently H or Me.

In particular embodiments, the produced alpha, beta-unsaturated compound can be acrylic acid or an acrylic ester having $R_2$=H, $R_3$=H and $R_4$=H.

Formation of alpha, beta-unsaturated compounds according to methods of the present invention can typically comprise a two step reaction process. In a first step, a first reagent can be an alpha-hydroxy compound having formula (II).

Formula (II):

A compound having formula (II) can be reacted with a second reagent, for example, an organic acid having formula (III).

Formula (III):

Reaction step one can form an alpha-acyloxy compound having formula (IV).

Formula (IV):

In a second step, the alpha-acyloxy compound having formula (IV) can be converted to an alpha, beta-unsaturated derivative comprising formula (I).

Methods of the present invention can include performing the first and second reaction steps in a single reaction vessel or alternatively performing the first step of the reaction in a first vessel and the second step of the reaction in a second vessel. Typically, a first reaction step comprising esterification to produce the alpha-acyloxy derivative of the alpha-hydroxy compound is performed in a first reaction vessel and the resulting alpha-acyloxy derivative is transferred to a second reaction vessel for further derivatization. Alternatively, the alpha-acyloxy derivative produced in the first step of the reaction can be collected and can optionally be purified. The alpha-acyloxy derivative can be utilized, for example, as a solvent or as a reagent in producing other useful compounds.

Figure 1:
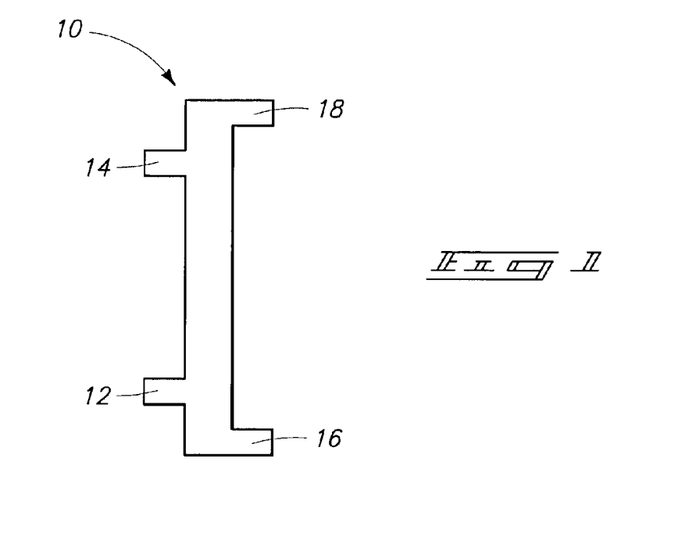
FIG. 1 depicts a vessel that can be utilized in performing methods according to one aspect of the present invention.

An exemplary vessel for utilization in production of the alpha-acyloxy derivative is shown in FIG. 1. A reaction vessel 10 can comprise a first inlet 12 and a second inlet 14. The carboxylic acid reagent can be introduced, for example, through inlet 12. The alpha-hydroxy reagent can be introduced, for example, through inlet 14. As shown in FIG. 1, inlet 12 can be disposed at a first elevation along reaction vessel 10 and second inlet 14 can be disposed at a second position elevationally higher along reaction vessel 10 relative to inlet 12. It is to be understood that the relative elevations of inlets 12 and 14 are not limited to the relationship shown in FIG. 1 and inlets 12 and 14 can be independently disposed at any elevation along reaction vessel 10. Alternatively, reaction vessel 10 can comprise a single inlet through which both the alpha-hydroxy reagent and the carboxylic acid reagent are introduced.

The carboxylic acid can preferably be introduced through first inlet 12 in vapor form. Accordingly, the carboxylic acid can be heated to at or above its boiling point prior to introduction into reaction vessel 10. Alternatively, the carboxylic acid reagent can be introduced in liquid form and reaction vessel 10 can be preheated, can be heated during the introduction of the carboxylic acid, can be heated subsequent to the introduction of the carboxylic acid, and/or can be maintained at a desired temperature subsequent to introduction of the carboxylic acid. Preferably, vessel 10 is maintained at a temperature sufficiently high to maintain the vapor form of the carboxylic acid. It can be advantageous to provide vaporized carboxylic acid to promote an upward directional flow of the vaporized acid within vessel 10.

The carboxylic acid utilized for derivatization of the alpha-hydroxy compound is not limited to any specific carboxylic acid. In other words, $R_5$ is not limited to any specific group and can be, for example, a linear or branched, saturated or unsaturated hydrocarbon group which can optionally contain one or more hetero atoms. Preferably $R_5$ comprises fewer than 20 carbons, and in particular embodiments can preferably be $CH_3$. In methods of the present invention that utilize a vessel such as exemplary vessel 10 shown in FIG. 1, the carboxylic acid utilized can preferably comprise a boiling point that is lower than the boiling point of the alpha-hydroxy compound utilized for the reaction.

The alpha-hydroxy compound can be introduced, for example, through second inlet 14 of reaction vessel 10, and can preferably be introduced in liquid form. The liquid form of the alpha-hydroxy compound can promote downward migration of the alpha-hydroxy compound within reaction vessel 10. Accordingly, reaction vessel 10 can be maintained at a temperature which is at or above the boiling point of the carboxylic acid and lower than the boiling point of the alpha-hydroxy compound to promote upward migration of the carboxylic acid vapor and downward migration of the alpha-hydroxy compound and the resulting alpha-acyloxy derivative. Such cross-flow can promote mixing of the two reagents and thereby promote the esterification reaction between the reagents to form the alpha-acyloxy derivative.

The alpha-hydroxy compound utilized as a reactant in vessel 10 is not limited to any particular compound. $R_1$, $R_2$, $R_3$ and $R_4$ can be as indicated above with respect to the desired alpha, beta-unsaturated product. In particular aspects the alpha-hydroxy compound can preferably be lactic acid or a lactic acid ester (wherein $R_2$, $R_3$ and $R_4$ are all hydrogen). As indicated, $R_1$ can preferably be hydrogen or any of those functional groups set forth above with respect to $R_1$.

The esterification reaction involved in reaction step one can produce the alpha-acyloxy derivative and one equivalent of water. Water can preferably be removed from the reaction, for example, providing one or more substances that can form an azeotrope with water, or addition of a substance that can chemically react with water. An exemplary compound which can react with water and thereby assist in the removal of water from the reaction is dicyclohexylcarbodiimide. Exemplary substances which can combine with water to form an azeotrope are benzene, hexane, chloroform, and acetic acid. Where a compound will be utilized as an azeotrope but is not a reagent in the reaction, it can be beneficial to utilize an azeotrope that is inert to both the carboxylic acid reagent, to the alpha-hydroxy reagent and to the alpha-acyloxy product.

Where acetic acid is used as a reactant to form an alpha-acetoxy product of step one, acetic acid can be utilized both as a reactant and to form an azeotrope for removal of water from reaction vessel 10. It can therefore be beneficial to utilize acetic acid as a reagent since it can serve as both the reagent and the azeotrope. The resulting azeotrope can be removed from vessel 10 through an outlet 18. As shown in FIG. 1, outlet 18 can preferably be disposed at or near an uppermost elevation of reaction vessel 10. A second outlet 16 can preferably be situated at or near a lowest elevation of reaction vessel 10. The product alpha-acyloxy derivative produced during step one of the overall reaction can be collected through outlet 16. It is to be understood that vessel 10 can comprise alternative configurations having outlets positioned at other locations than those depicted if FIG. 1, or can comprise a single outlet for common removal of products and/or reagents.

The rate of the esterification reaction to form the alpha-acyloxy derivative in step one can be enhanced by, for example, providing a catalyst in reaction vessel 10. Exemplary catalysts for utilization in step one can comprise, for example, a strong acid catalyst such as sulfuric acid, polysulfonic acid, polyphosphoric acid or a solid acid catalyst. It can be advantageous to utilize a solid acid catalyst such as an ion exchange resin, nafion or a zeolite as a catalyst in reaction vessel 10 to allow a continuous reaction without a continuous feed of a liquid acid catalyst. Alternatively, a liquid catalyst can be continuously fed to reaction vessel 10 or a batch process method can be conducted utilizing a liquid acid catalyst, a solid acid catalyst or combinations thereof.

The esterification reaction in step one can also be enhanced by utilizing an excess reactant, such as the carboxylic acid. A reagent excess can be utilized in combination with one or more of the acid catalysts discussed above. It is to be noted that removal of water by, for example, addition of an azeotrope can also enhance the rate of esterification. Accordingly, it can be advantageous to utilize a combination of two or more rate enhancers selected from the group consisting of excess reactant, product removal, and catalysis.

Reaction step one can be performed under vacuum, at atmospheric or under pressure. The temperature of the reaction can be adjusted accordingly.

Where methods of the present invention involve utilization of an azeotrope, it can be advantageous to provide one or more of the reagents in anhydrous form. For example, where the carboxylic acid reagent is acetic acid, such can be provided in glacial form. Additionally, where the alpha-hydroxyl compound is an ester, such ester can be provided in anhydrous form.

The second step of the overall reaction involves conversion of the alpha-acyloxy derivative produced in step one into the corresponding alpha, beta-unsaturated acid or ester. For methods utilizing, for example, a reactive distillation column such as that shown in FIG. 1, the alpha-acyloxy compound produced in step one can be collected through outlet 16 and transferred to a second reaction vessel wherein the step two conversion will take place.

Transforming the alpha-acyloxy derivative into an alpha, beta-unsaturated product can typically comprise a pyrolysis reaction, with production of the alpha, beta-unsaturated derivative accompanied by liberation of one equivalent of the carboxylic acid utilized for esterification during step 1. The liberated carboxylic acid can optionally be collected, dried and/or recycled.

Although the pyrolysis step can be performed without a catalyst, it can be preferable to utilize a catalyst such as a weak acid catalyst during the pyrolysis step. Exemplary weak acid catalysts include but are not limited to sulfate salts and phosphate salts. In particular embodiments, the weak acid catalyst can comprise calcium sulfate. The acid catalyst can be provided to a concentration suitable to catalyze the pyrolysis reaction. It can be advantageous to provide a catalyst during the pyrolysis step to allow lower pyrolysis temperatures. Providing a catalyst during pyrolysis can also improve yields of the resulting alpha, beta-unsaturated product.

In order to alleviate or avoid fouling or contamination of the catalyst utilized in the pyrolysis step, it can be advantageous to decrease or eliminate impurities present in the alpha-acyloxy sample prior to introducing the sample to the presence of the catalyst. Where the pyrolysis reactor is distinct from the reactor in which the esterification reaction was performed, a pre-reactor can be utilized prior to introducing the alpha-acyloxy compound into the pyrolysis reactor. As an example, where the alpha-hydroxy reagent utilized in step one comprises lactic acid or a lactic acid ester, use of a pre-reactor after collection of the initial alpha-acyloxy product can remove impurities such as lactide and lactide breakdown products, prior to introducing the 2-acyloxy lactic acid or ester sample into the pyrolysis reactor. Conventional pre-reactors are available for purposes of the present invention as will be recognized by one of ordinary skill in the art.

The alpha, beta-unsaturated compound produced during the pyrolysis step can be an acid or an ester as discussed above. Optionally, an esterification or trans-esterification reaction can be used to replace the initial group $R_1$ with $R_6$, thereby producing a desired ester derivative having formula (V).

Formula (V):

As indicated above, $R_6$ can be any group desired. Preferably, $R_6$ is a linear or branched, saturated or unsaturated hydrocarbon group which can optionally contain one or more hetero atoms, and in particular aspects can be selected from the group consisting of $CH_3$, $CH_2CH_3$, 2-ethylhexyl, and $(CH_2)_xCH_3$, wherein x is from 2 to 19. Conversion of the alpha, beta-unsaturated product from the pyrolysis reaction to the desired ester can utilize conventional esterification techniques. Such conversion can occur within the same reactor in which the pyrolysis was performed or can occur in a separate reactor.

Figure 2:
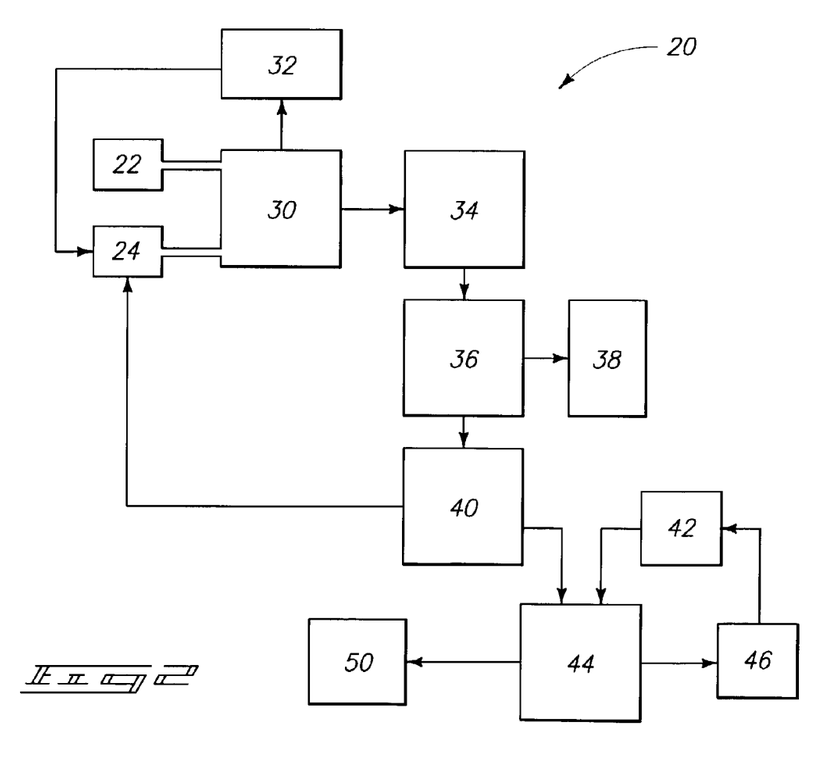
FIG. 2 is a flow diagram showing a processing system that can be used in performing particular aspects of the present invention.

An exemplary system which can be utilized for producing any of the initial alpha-acyloxy product, the initial alpha, beta-unsaturated acid or ester product, or an esterified or trans-esterified alpha, beta-unsaturated product is described generally with respect to FIG. 2. A first reactant source 22 can be provided to supply a first reactant to a first reaction vessel 30. The first reactant source can supply any of the alpha-hydroxy acids and esters discussed above. A second reactant source 24 can supply a second reactant to reaction vessel 30. Exemplary second reactants can be any of those carboxylic acid compounds discussed above.

Reaction vessel 30 can comprise, for example, a column such as the reactive distillation column shown in FIG. 1. Alternatively, reaction vessel 30 can comprise an alternative column structure or a non-column reactor. A catalyst can be provided in reaction vessel 30 and can comprise any of the step one catalysts discussed above.

In embodiments wherein an excess of the carboxylic acid reagent is utilized in reaction step one, a recovery system 32 can be provided for recovery of the non-reacted carboxylic acid. The recovered carboxylic acid can then be recycled back to reactant source 24. Where an azeotrope is utilized to remove water from the reaction, recovery system 32 can comprise, for example, a drying compound or molecular sieve capable of removing some or all of the water from the collected azeotrope.

The alpha-acyloxy acid or ester produced in reaction vessel 30 can be transferred to a second reaction vessel 34 in which the pyrolysis reaction can be conducted. The pyrolysis reaction can convert the transferred alpha-acyloxy acid or ester to the corresponding alpha, beta-unsaturated acid or ester accompanied by liberation of one equivalent of carboxylic acid. A catalyst, such as any of the pyrolysis catalysts discussed above, can optionally be provided in pyrolysis reactor 34.

The pyrolysis products can be transferred to a flash tank 36 for removal of byproducts produced during the previous esterification and/or pyrolysis reactions. For example, when the carboxylic acid utilized for the initial esterification in reactor 30, byproducts may be generated during the formation of the alpha, beta-unsaturated acid or ester product. Some or all of the byproducts generated can be removed in flash tank 36 and can be transferred for example, to a waste container 38.

As shown in FIG. 2, the liberated carboxylic acid and the alpha, beta-unsaturated acid or ester can be transferred from flash tank 36 to a distillation reactor 40. Alternatively, the regenerated carboxylic acid and alpha, beta-unsaturated acid or ester can be transferred directly from pyrolysis reactor 34 into distillation reactor 40 without utilization of flash tank 36.

Distillation reactor 40 can be utilized to remove some or all of regenerated carboxylic acid which can be recycled back to reagent source 24. The distilled alpha, beta-unsaturated acid or ester can be recovered from distillation reactor 40. In particular embodiments, the alpha, beta-unsaturated product can be recovered in anhydrous form.

Optionally, the alpha, beta-unsaturated acid or ester from distillation reactor 40 can undergo further reaction to esterify or trans-esterify the distilled compound to produce a desired ester derivative in an independent reaction vessel 44. Reaction vessel 44 can be, for example, a reactive distillation column such as vessel 10 shown in FIG. 1. Accordingly, an esterification reactant such as an alcohol can be introduced from a reagent source 42 through a first inlet disposed at a first elevation on reaction vessel 44. The alpha, beta-unsaturated acid or ester can be introduced into reaction vessel 44 for example, through a second inlet positioned at a second elevation which is elevationally above the first inlet. Using conventional esterification conditions and an appropriate alcohol, the introduced alpha, beta-unsaturated acid or ester can be converted into the desired ester derivative. Water and non-reacted alcohol can be recovered and introduced into a distillation reactor 46 for example, and the resulting distilled alcohol can be recycled back into source 42.

The resulting esterified or trans-esterified alpha, beta-unsaturated compound can be collected from vessel 44 and can optionally be distilled in a distillation reactor 50 to remove at least some of any byproducts present in the collected sample.

In alternative embodiments, an alpha, beta-unsaturated ester produced in reaction step two can be subsequently hydrolyzed to produce an alpha, beta-unsaturated acid using conventional ester hydrolysis methods.

EXAMPLE 1

Batch Production of Alpha-Acyloxy Products

Anhydrous methyl lactate (1 ml) was combined with glacial acetic acid (15 ml) in a reaction vessel to form a solution. Concentrated sulfuric acid (0.1 ml) was added and the resulting solution was heated to a reflux temperature of about 73° C. at a pressure of 150 mm Hg. The resulting condensate was dripped into a soxlet containing $SiO_2$ (disposed between the reaction vessel and a reflux condenser) to remove water from the vapor and recycle dried acetic acid back into the reaction vessel. After one hour, the reaction was terminated by cooling the solution to room temperature and venting the vessel to atmospheric pressure. Nuclear magnetic resonance (NMR) analysis of the solution indicated a product ratio of 2-acetoxy propionic acid to its methyl ester (methyl 2-acetoxy propionate) of about 1:1. Methyl acetate was also formed as a byproduct. The combined acid and methyl ester product yield was approximately 95% of theoretical (estimated by NMR spectra). The NMR analysis further indicated an apparently complete consumption of the starting methyl lactate.

In an independent experiment, a molar equivalent of lactic acid was utilized as a starting reagent in place of methyl lactate. The lactic acid reagent utilized was an aqueous solution containing approximately 85% lactic acid, by weight. The reaction conditions were otherwise as indicated above. NMR analysis of the resulting product material indicated a 2-acetoxy propionic acid product yield of greater than about 90% with some dimer or polymer byproduct formation apparent.

The results of the batch production of and methyl 2-acetoxy propionate and 2-acetoxy propionic acid indicate that acetic acid azeotropically removes water from the reaction.

EXAMPLE 2

Production of Alpha-Acyloxy Products Utilizing Continuous Flow Simulation

In a distillation reactor at atmospheric pressure, an acid solution formed by combining 30 ml of glacial acetic acid with 0.5 ml concentrated sulfuric acid was maintained at approximately 114° C. A reactant solution was prepared by combining 5.0 ml of an 85% lactic acid solution, by weight (15% water) with 20 ml of glacial acetic acid, and was added dropwise to the distillation reactor. The resulting distillate was collected and analyzed by NMR. After 1 hour, the 2-acetoxy propionic acid product yield was greater than about 90%. A small amount of dimer or polymer was also detected.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

What is claimed is:

1. A method of forming an alpha-acetoxy compound comprising:

providing a reactant comprising an alpha-hydroxyl group and having the formula wherein $R_1$ is selected from the group consisting of H and hydrocarbons containing from 1 to 20 carbon atoms, wherein each of $R_2$, $R_3$ and $R_4$ are independently selected from the group consisting of H, hydrocarbons containing from 1 to 20 carbon atoms, and heteroatom substituted hydrocarbons containing from 1 to 20 carbon atoms, and wherein if $R_2$ is methyl, at least one of $R_4$ and $R_3$ is other than H;
providing acetic acid;
reacting the alpha-hydroxyl group with the acetic acid to form an alpha-acetoxy compound; and
collecting the alpha-acetoxy compound.

2. The method of claim 1 wherein the providing acetic acid comprises providing glacial acetic acid.

3. The method of claim 1 wherein the reactant comprising an alpha-hydroxyl group is provided in anhydrous form.

4. A method of derivitizing an alpha-hydroxy group comprising:
providing a reaction vessel having a first and second inlets and an outlet, the first inlet being at a first elevation and the second inlet being at a second elevation; that is higher than the first elevation;
introducing an azeotrope forming substance through the first inlet, the azeotrope forming substance having the ability to form an azeotrope with water, the azeotrope forming substance flowing elevationally upward after introduction through the first inlet;
introducing a compound comprising an alpha-hydroxyl group through the second inlet;
providing a catalytic acid within the reaction vessel;
introducing a reactant having a carboxylic acid group into the reaction vessel;
reacting the alpha-hydroxy group with the carboxylic acid group to form an alpha-acyloxy product; and
collecting the alpha-acyloxy product through the outlet.

5. The method of claim 4 wherein the catalytic acid is a solid.

6. The method of claim 4 wherein the reactant having the carboxylic acid group comprises fewer than 20 carbon atoms.

7. The method of claim 4 wherein the reactant comprising the carboxylic acid group is acetic acid.

8. The method of claim 4 wherein the azeotrope forming substance and the reactant having a carboxylic acid group are the same.

9. The method of claim 4 wherein the compound comprising an alpha-hydroxyl group migrates elevationally downward after introduction through the second inlet and wherein the outlet comprises an outlet positioned at a third elevation, the third elevation being at or below the first elevation.

10. The method of claim 9 wherein the outlet is a first outlet and wherein the reaction vessel comprises a second outlet positioned at a fourth elevation, and wherein a portion of the azeotrope forming substance is collected through the second outlet.

11. A method of derivatizing an alpha-hydroxy acid comprising:
providing an alpha-hydroxy acid in liquid form into a first vessel;
providing gaseous acetic acid to the first vessel;
reacting the acetic acid with the alpha-hydroxy acid to form an alpha-acetoxy acid;
transferring the alpha-acetoxy acid to a second vessel; and
performing a pyrolysis reaction within the second vessel, the pyrolysis reaction converting the alpha-acetoxy acid to an alpha, beta-unsaturated acid.

12. The method of claim 1 further comprising collecting the alpha, beta-unsaturated acid from the second vessel in an anhydrous form.

13. The method of claim 1 further comprising converting the alpha, beta-unsaturated acid to an alpha, beta-unsaturated ester.

14. The method of claim 13 wherein the alpha, beta-unsaturated ester comprises a member of the group consisting of n-butyl ester and 2-ethylhexyl ester.

15. A method of forming a compound having a formula (I)

comprising:
providing a directional flow of a first reactant having a formula (II) into a reaction chamber providing a cross-flow of a second reactant having the formula (III)

providing a catalyst;
in the presence of the catalyst, reacting the first and second reactants to form an initial product having the formula (IV)

and
transforming the initial product into the compound having formula(I), wherein $R_1$ is selected from the group consisting of H and hydrocarbons containing from 1 to 20 carbon atoms, and wherein each of $R_2$, $R_3$, $R_4$ and $R_5$ are independently selected from the group consisting of H, hydrocarbons containing from 1 to 20 carbon atoms, and heteroatom substituted hydrocarbons containing from 1 to 20 carbon atoms.

16. The method of claim 15 wherein the catalyst is selected from the group consisting of sulfuric acid, polysulfonic acid, polyphosphoric acid and a solid acid catalyst.

17. The method of claim 15 wherein the providing the second reactant comprises providing the second reactant in gaseous form.

18. The method of claim 15 further comprising collecting the compound, wherein the providing the first reactant comprises providing a molar quantity of the first reactant and wherein the collecting the compound comprises collecting a molar quantity of the compound, the molar quantity of the compound being about 90% of the molar quantity of the first reactant.

19. The method of claim 15 further comprising:
providing a reaction column comprising:
a first inlet at a first elevation;
a second inlet at a second elevation;
a product outlet; and
collecting the initial product through the product outlet;
wherein the providing the first reactant comprises providing the first reactant through the first inlet, and the providing the second reactant comprises providing the second reactant through the second inlet.

20. The method of claim 19 wherein the first elevation is at a higher elevation on the column than the second elevation.

21. The method of claim 19 wherein the column further comprises a recovery outlet elevationally higher than the product outlet, wherein the providing the second reactant comprises providing an initial amount, and wherein a portion of the initial amount is recovered through the recovery outlet.

22. The method of claim 19 wherein the transforming comprises:
providing the initial product to a reactor; and
performing a pyrolysis reaction within the reactor.

23. The method of claim 22 wherein $R_5=CH_3$ and wherein the pyrolysis reaction produces acetic acid.

24. The method of claim 19 wherein the catalyst comprises a solid acid catalyst.

25. A method of producing an acrylate ester comprising:
providing a first reactant comprising lactic acid in the presence of water;
providing a carboxylic acid;
esterifying the carboxylic acid to form an alpha-acyloxy derivative of the first reactant;
converting the alpha-acyloxy derivative to the corresponding acrylic acid; and
converting the acrylic acid to an acrylate ester.

26. A method of forming a compound having a formula comprising:
providing a first reactant to a first vessel, through a first inlet, the first reactant having a formula providing a second reactant to the first vessel through a second inlet disposed elevationally below the first inlet, the second reactant having the formula providing a catalyst within the first vessel;
in the presence of the catalyst, reacting the first and second reactants to form an initial product having the formula transferring the initial product to a second vessel; and
after the transferring, transforming the initial product into the compound, wherein $R_1$ is selected from the group consisting of H and hydrocarbons containing from 1 to 20 carbon atoms, wherein each of $R_2$, $R_3$, $R_4$, $R_5$ and $R_6$ are independently selected from the group consisting of H, hydrocarbons containing from 1 to 20 carbon atoms, and heteroatom substituted hydrocarbons containing from 1 to 20 carbon atoms.

27. The method of claim 26 wherein $R_6 \neq R_1$, and wherein $R_6$ is selected from the group consisting of methyl, ethyl, n-butyl and 2-ethylhexyl.

28. The method of claim 26 wherein $R_6 \neq R_1$, and wherein $R_1$ is selected form the group consisting of $CH_3$, $CH_2CH_3$, and H.

29. The method of claim 26 wherein the transforming comprises:
forming an alpha, beta-unsaturated compound in the second vessel, the alpha, beta-unsaturated compound having the formula distilling the alpha, beta-unsaturated compound; and
after the distilling, reacting the alpha, beta-unsaturated compound with a compound of the formula $HOR_6$ to esterify at least some of the alpha, beta-unsaturated compound to replace $R_1$ with $R_6$.

30. A process for forming an acrylate comprising:
introducing an amount of one of lactic acid or a lactic acid ester into a first vessel;
introducing a molar excess of acetic acid relative to the amount of lactic acid or lactic acid ester into the first vessel,
reacting the lactic acid or lactic acid ester with a first portion of the acetic acid in the presence of a first catalyst to produce the corresponding 2-acetoxy propionic acid or ester;
recycling a non-reacted portion of the acetic acid:
transferring the 2-acetoxy propionic acid or ester to a second vessel;
providing a second catalyst in the second vessel;
within the second vessel, liberating acetic acid from the 2-acetoxy propionic acid or ester to produce the corresponding acrylic acid or first acrylate ester;
removing the liberated acetic acid by distillation of the acrylic acid or first acrylate ester;
after the removing, mixing the acrylic acid or first acrylate ester with an alcohol; and
esterifying the acrylic acid or trans-esterifying the first acrylate ester by reaction with the alcohol to form a second acrylate ester.

31. The method of claim 30 wherein the alcohol is selected from the group consisting of butanol and 2-ethyl hexanol.

32. The method of claim 30 wherein the esterifying the acid or trans-esterifying the acrylate ester by reaction with the alcohol comprises reactive distillation and wherein an unreacted portion of the alcohol is collected and recycled.

33. The method of claim 30 wherein the non-reacted portion of acetic acid forms an azeotrope in the first vessel and wherein the recycling the non-reacted portion comprises collecting and drying the non-reacted portion to remove at least some of any water present in the collected non-reacted portion.

34. The method of claim 30 wherein the second catalyst comprises calcium sulfate.

* * * * *

UNITED STATES PATENT AND TRADEMARK OFFICE
CERTIFICATE OF CORRECTION

| | | |
|---|---|---|
| PATENT NO. | : 6,992,209 B2 | |
| APPLICATION NO. | : 10/315404 | |
| DATED | : January 31, 2006 | |
| INVENTOR(S) | : Lilga et al. | |

It is certified that error appears in the above-identified patent and that said Letters Patent is hereby corrected as shown below:

Column 3, Line 54 – Replace "be-heated" with --be preheated--.

Column 4, Line 50 – Replace "A shown" with --As shown--.

Column 4, Line 58 – Replace "if FIG." with --in FIG.--.

Delete claims in Column 8 line 50 through Column 14 lines 20 and insert the following claims as follows.

--1. (Currently amended) A method of forming an alpha-acetoxy compound comprising:

providing a reactant comprising an alpha-hydroxyl group and having the formula

;

wherein $R_1$, is selected from the group consisting of H and hydrocarbons containing from 1 to 20 carbon atoms, wherein each of $R_2$, $R_3$ and $R_4$ are independently selected from the group consisting of H, hydrocarbons containing from 1 to 20 carbon atoms, and heteroatom substituted hydrocarbons containing from 1 to 20 carbon atoms, and wherein if $R_2$ is methyl, at least one of $R_4$ and $R_3$ is other than H;

providing acetic acid;

reacting the alpha-hydroxyl group with the acetic acid to form an alpha-acetoxy compound; and collecting the alpha-acetoxy compound.

UNITED STATES PATENT AND TRADEMARK OFFICE
CERTIFICATE OF CORRECTION

PATENT NO. : 6,992,209 B2
APPLICATION NO. : 10/315404
DATED : January 31, 2006
INVENTOR(S) : Lilga et al.

It is certified that error appears in the above-identified patent and that said Letters Patent is hereby corrected as shown below:

2. (Original) The method of claim 1 wherein the providing acetic acid comprises providing glacial acetic acid.

3. (Original) The method of claim 1 wherein the reactant comprising an alpha-hydroxyl group is provided in anhydrous form.

4. (Currently amended) A method of derivitizing an alpha-hydroxy group comprising:

providing a reaction vessel having a first and second inlets and an outlet, the first inlet being at a first elevation and the second inlet being at a second elevation; that is higher than the first elevation;

introducing an azeotrope forming substance through the first inlet, the azeotrope forming substance having the ability to form an azeotrope with water, the azeotrope forming substance flowing elevationally upward after introduction through the first inlet;

introducing a compound comprising an alpha-hydroxyl group through the second inlet;

providing a catalytic acid within the reaction vessel;

introducing a reactant having a carboxylic acid group into the reaction vessel;

reacting the alpha-hydroxy group with the carboxylic acid group to form an alpha-acyloxy product; and     collecting the alpha-acyloxy product through the outlet.

UNITED STATES PATENT AND TRADEMARK OFFICE
CERTIFICATE OF CORRECTION

PATENT NO. : 6,992,209 B2
APPLICATION NO. : 10/315404
DATED : January 31, 2006
INVENTOR(S) : Lilga et al.

It is certified that error appears in the above-identified patent and that said Letters Patent is hereby corrected as shown below:

5. (Original) The method of claim 4 wherein the catalytic acid is a solid.

6. (Original) The method of claim 4 wherein the reactant having the carboxylic acid group comprises fewer than 20 carbon atoms.

7. (Original) The method of claim 4 wherein the reactant comprising the carboxylic acid group is acetic acid.

8. (Original) The method of claim 4 wherein the azeotrope forming substance and the reactant having a carboxylic acid group are the same.

9. (Currently amended) The method of claim 4 wherein the compound comprising an alpha-hydroxyl group migrates elevationally downward after introduction through the second inlet and wherein the outlet comprises an outlet positioned at a third elevation, the third elevation being at or below the first elevation.

10. (Original) The method of claim 9 wherein the outlet is a first outlet and wherein the reaction vessel comprises a second outlet positioned at a fourth elevation, and wherein a portion of the azeotrope forming substance is collected through the second outlet.

UNITED STATES PATENT AND TRADEMARK OFFICE
CERTIFICATE OF CORRECTION

PATENT NO. : 6,992,209 B2
APPLICATION NO. : 10/315404
DATED : January 31, 2006
INVENTOR(S) : Lilga et al.

It is certified that error appears in the above-identified patent and that said Letters Patent is hereby corrected as shown below:

11. (Currently amended) A method of derivatizing an alpha-hydroxy acid comprising:

providing an alpha-hydroxy acid in <u>liquid form into</u> a first vessel;

providing <u>gaseous</u> acetic acid to the first vessel;

reacting the acetic acid with the alpha-hydroxy acid to form an alpha-acetoxy acid;

transferring the alpha-acetoxy acid to a second vessel; and performing a pyrolysis reaction within the second vessel, the pyrolysis reaction converting the alpha-acetoxy acid to an alpha, beta-unsaturated acid.

12. (Currently amended) A method of forming a compound having a formula <u>(I)</u>

, comprising:

providing <u>a directional flow of a</u> first reactant having a formula <u>(II) into a reaction chamber</u>

;

providing a <u>cross-flow of a</u> second reactant having the formula <u>(III)</u>

UNITED STATES PATENT AND TRADEMARK OFFICE
CERTIFICATE OF CORRECTION

PATENT NO. : 6,992,209 B2
APPLICATION NO. : 10/315404
DATED : January 31, 2006
INVENTOR(S) : Lilga et al.

It is certified that error appears in the above-identified patent and that said Letters Patent is hereby corrected as shown below:

providing a catalyst;

in the presence of the catalyst, reacting the first and second reactants to form an initial product having the formula (IV)

; and transforming the initial product into the compound having formula (I), wherein $R_1$ is selected from the group consisting of H and hydrocarbons containing from 1 to 20 carbon atoms, and wherein each of $R_2$, $R_3$, $R_4$ and $R_5$ are independently selected from the group consisting of H, hydrocarbons containing from 1 to 20 carbon atoms, and heteroatom substituted hydrocarbons containing from 1 to 20 carbon atoms.

13. (Original) The method of claim 12 wherein the catalyst is selected from the group consisting of sulfuric acid, polysulfonic acid, polyphosphoric acid and a solid acid catalyst.

14. (Original) The method of claim 12 wherein the providing the second reactant comprises providing the second reactant in gaseous form.

UNITED STATES PATENT AND TRADEMARK OFFICE
CERTIFICATE OF CORRECTION

| | |
|---|---|
| PATENT NO. | : 6,992,209 B2 |
| APPLICATION NO. | : 10/315404 |
| DATED | : January 31, 2006 |
| INVENTOR(S) | : Lilga et al. |

It is certified that error appears in the above-identified patent and that said Letters Patent is hereby corrected as shown below:

15. (Original) The method of claim 12 further comprising collecting the compound, wherein the providing the first reactant comprises providing a molar quantity of the first reactant and wherein the collecting the compound comprises collecting a molar quantity of the compound, the molar quantity of the compound being about 90% of the molar quantity of the first reactant.

16. (Original) The method of claim 12 further comprising:

providing a reaction column comprising;

a first inlet at a first elevation;

a second inlet at a second elevation;

a product outlet; and collecting the initial product through the product outlet; wherein the providing the first reactant comprises providing the first reactant through the first inlet, and the providing the second reactant comprises providing the second reactant through the second inlet.

17. (Original) The method of claim 16 wherein the first elevation is at a higher elevation on the column than the second elevation.

18. (Original) The method of claim 16 wherein the column further comprises a recovery outlet elevationally higher than the product outlet, wherein the providing the second reactant comprises providing an initial amount, and wherein a portion of the initial amount is recovered through the recovery outlet.

UNITED STATES PATENT AND TRADEMARK OFFICE
CERTIFICATE OF CORRECTION

PATENT NO. : 6,992,209 B2
APPLICATION NO. : 10/315404
DATED : January 31, 2006
INVENTOR(S) : Lilga et al.

It is certified that error appears in the above-identified patent and that said Letters Patent is hereby corrected as shown below:

19. (Original) The method of claim 16 wherein the transforming comprises:

providing the initial product to a reactor, and performing a pyrolysis reaction within the reactor.

20. (Original) The method of claim 19 wherein $R_5 = CH_3$ and wherein the pyrolysis reaction produces acetic acid.

21. (Original) The method of claim 16 wherein the catalyst comprises a solid acid catalyst.

22. (Currently amended) A method of producing an acrylate ester comprising:

providing a first reactant comprising ~~at least one of~~ lactic acid ~~and a lactic acid ester~~ in the presence of water;

providing a carboxylic acid;

esterifying the carboxylic acid to form an alpha-acyloxy derivative of the first reactant;

converting the alpha-acyloxy derivative to the corresponding acrylic acid ~~or first acrylate ester~~; and converting the acrylic acid to an ~~or first acrylate ester to a second~~ acrylate ester.

UNITED STATES PATENT AND TRADEMARK OFFICE
CERTIFICATE OF CORRECTION

| | | |
|---|---|---|
| PATENT NO. | : 6,992,209 B2 | Page 8 of 11 |
| APPLICATION NO. | : 10/315404 | |
| DATED | : January 31, 2006 | |
| INVENTOR(S) | : Lilga et al. | |

It is certified that error appears in the above-identified patent and that said Letters Patent is hereby corrected as shown below:

23. (Currently amended) A method of forming a compound having a formula comprising:

providing a first reactant to a first vessel <u>through a first inlet</u>, the first reactant having a formula  ;

providing a second reactant to the first vessel <u>through a second inlet disposed elevationally below the first inlet, the second reactant</u> having the formula providing a catalyst within the first vessel;

in the presence of the catalyst, reacting the first and second reactants to form an initial product having the formula

;

transferring the initial product to a second vessel; and

UNITED STATES PATENT AND TRADEMARK OFFICE
CERTIFICATE OF CORRECTION

PATENT NO. : 6,992,209 B2
APPLICATION NO. : 10/315404
DATED : January 31, 2006
INVENTOR(S) : Lilga et al.

It is certified that error appears in the above-identified patent and that said Letters Patent is hereby corrected as shown below:

after the transferring, transforming the initial product into the compound, wherein $R_1$ is selected from the group consisting of H and hydrocarbons containing from 1 to 20 carbon atoms, wherein each of $R_2$, $R_3$, $R_4$, $R_5$ and $R_6$ are independently selected from the group consisting of H, hydrocarbons containing from 1 to 20 carbon atoms, and heteroatom substituted hydrocarbons containing from 1 to 20 carbon atoms.

24. (Original) The method of claim 23 wherein $R_6 \neq R_1$, and wherein $R_6$ is selected from the group consisting of methyl, ethyl, n-butyl and 2-ethylhexyl.

25. (Original) The method of claim 23 wherein $R_6 \neq R_1$, and wherein $R_1$ is selected from the group consisting of $CH_3$, $CH_2CH_3$, and H.

26. (Original) The method of claim 23 wherein the transforming comprises:

forming an alpha, beta-unsaturated compound in the second vessel, the alpha, beta-unsaturated compound having the formula

;

distilling the alpha, beta-unsaturated compound; and after the distilling, reacting the alpha, beta-unsaturated compound with a compound of the formula $HOR_6$ to esterify at least some of the alpha, beta-unsaturated compound to replace $R_1$ with $R_6$.

UNITED STATES PATENT AND TRADEMARK OFFICE
CERTIFICATE OF CORRECTION

| | |
|---|---|
| PATENT NO. | : 6,992,209 B2 |
| APPLICATION NO. | : 10/315404 |
| DATED | : January 31, 2006 |
| INVENTOR(S) | : Lilga et al. |

It is certified that error appears in the above-identified patent and that said Letters Patent is hereby corrected as shown below:

27. (Original) A process for forming an acrylate comprising:

introducing an amount of one of lactic acid or a lactic acid ester into a first vessel;

introducing a molar excess of acetic acid relative to the amount of lactic acid or lactic acid ester into the first vessel, reacting the lactic acid or lactic acid ester with a first portion of the acetic acid in the presence of a first catalyst to produce the corresponding 2-acetoxy propionic acid or ester;

recycling a non-reacted portion of the acetic acid:

transferring the 2-acetoxy propionic acid or ester to a second vessel;

providing a second catalyst in the second vessel;

within the second vessel, liberating acetic acid from the 2-acetoxy propionic acid or ester to produce the corresponding acrylic acid or first acrylate ester;

removing the liberated acetic acid by distillation of the acrylic acid or first acrylate ester;

after the removing, mixing the acrylic acid or first acrylate ester with an alcohol; and esterifying the acrylic acid or trans-esterifying the first acrylate ester by reaction with the alcohol to form a second acrylate ester.

UNITED STATES PATENT AND TRADEMARK OFFICE
CERTIFICATE OF CORRECTION

PATENT NO. : 6,992,209 B2
APPLICATION NO. : 10/315404
DATED : January 31, 2006
INVENTOR(S) : Lilga et al.

It is certified that error appears in the above-identified patent and that said Letters Patent is hereby corrected as shown below:

28. (Original) The method of claim 27 wherein the alcohol is selected from the group consisting of butanol and 2-ethyl hexanol.

29. (Original) The method of claim 27 wherein the esterifying the acid or trans-esterifying the acrylate ester by reaction with the alcohol comprises reactive distillation and wherein an unreacted portion of the alcohol is collected and recycled.

30. (Original) The method of claim 27 wherein the non-reacted portion of acetic acid forms an azeotrope in the first vessel and wherein the recycling the non-reacted portion comprises collecting and drying the non-reacted portion to remove at least some of any water present in the collected non-reacted portion.

31. (Original) The method of claim 27 wherein the second catalyst comprises calcium sulfate.--

Signed and Sealed this

Seventeenth Day of April, 2007

JON W. DUDAS
*Director of the United States Patent and Trademark Office*